US00PP20400P2

(12) United States Plant Patent
Van Zanten

(10) Patent No.: US PP20,400 P2
(45) Date of Patent: Oct. 6, 2009

(54) ***CHRYSANTHEMUM* PLANT NAMED 'GG GOSTRNG 08'**

(50) Latin Name: *Chrysanthemum morifolium*
Varietal Denomination: GG GOSTRNG 08

(75) Inventor: Leo Van Zanten, Oxnard, CA (US)

(73) Assignee: Grolink Plant Company, Oxnard, CA (US)

( * ) Notice: Subject to any disclaimer, the term of this patent is extended or adjusted under 35 U.S.C. 154(b) by 0 days.

(21) Appl. No.: 12/218,819

(22) Filed: Jul. 18, 2008

(51) Int. Cl.
*A01H 5/00* (2006.01)

(52) U.S. Cl. ..... Plt./286

(58) Field of Classification Search ..... Plt./286, Plt./297

See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by large daisy type inflorescences, consistent flowering response to short days, blooming consistently after 52 days of short day length, lavender pink ray florets, yellow disc with a green eye, and a free branching habit.

1 Drawing Sheet

Latin name of the genus and species: *Chrysanthemum morifolium.*

Variety denomination: 'GG GOSTRNG 08'.

BACKGROUND OF THE INVENTION

The new cultivar 'GG GOSTRNG 08' is a product of a cross between the male parent 'Davis' (U.S. Plant Pat. No. 7,325) and the female parent 'PE0901' (unpatented). The new cultivar was discovered and selected by Leo Van Zanten in July of 2003 in Oxnard, Calif.

Asexual reproduction of the new cultivar 'GG GOSTRNG 08' by terminal cuttings was performed in Oxnard, Calif., and has shown that the unique features of this new cultivar are stable and reproduced true to type on successive generations.

SUMMARY OF THE INVENTION

The cultivar 'GG GOSTRNG 08' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG GOSTRNG 08.' These characteristics in combination distinguish 'GG GOSTRNG 08' as a new and distinct *Chrysanthemum* cultivar:

1. Large, lavender pink, daisy-type inflorescences;
2. Yellow disc with a green eye;
3. Free branching habit; and
4. Consistent flowering response to short days, blooming consistently after 52 days of short day length.

Plants of the new cultivar 'GG GOSTRNG 08' are similar to plants of the male parent variety, 'Davis' in most horticultural characteristics, however plants of the new cultivar 'GG GOSTRNG 08' are shorter. Also, the new cultivar 'GG GOSTRNG 08' has a larger inflorescence diameter and longer inflorescence longevity. Additionally, the disc florets of 'GG GOSTRNG 08' are more green in color and the new cultivar has more flowers per stem than the male parent. Finally, 'GG GOSTRNG 08' has a shorter response time.

Plants of the new cultivar 'GG GOSTRNG 08' are similar to plants of the female parent variety, 'PE0901' in most horticultural characteristics, however plants of the new cultivar 'GG GOSTRNG 08' are shorter but have a wider plant spread. Also, the new cultivar 'GG GOSTRNG 08' has a smaller inflorescence diameter. Additionally, the ray florets of 'GG GOSTRNG 08' are a lighter pink than the female parent. Finally, 'GG GOSTRNG 08' has a shorter response time.

In comparison to the commercially available variety 'Raspberry Ice' (U.S. Plant Pat. No. 10,390), 'GG GOSTRNG 08' is shorter and wider. Additionally, the new variety 'GG GOSTRNG 08' has a smaller inflorescence diameter and a more pronounced green heart in the yellow disc. Finally, the ray florets of 'GG GOSTRNG 08' are a lighter red-purple compared to the darker greyed-purple of the comparable variety.

BRIEF DESCRIPTION OF THE PHOTOGRAPH

The accompanying photograph illustrates in full color a typical plant of 'GG GOSTRNG 08' grown in a 6 inch container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG GOSTRNG 08' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'GG GOSTRNG 08.'
Commercial classification: Pot-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 14 cm.
Plant spread: Approximately 30 cm.
Growth rate: Moderate.
Branching characteristics: Free Branching.
Length of lateral branches: Approximately 8 cm.
Number of leaves per lateral branch: Approximately 15.
Age of plant described: Approximately 100 days.

FOLIAGE

Leaf:
- *Arrangement.*—Alternate single.
- *Average length.*—Approximately 4 cm.
- *Average width.*—Approximately 2.8 cm.
- *Shape of blade.*—Ovate.
- *Apex.*—Acuminate.
- *Base.*—Attenuate.
- *Attachment.*—Stalked.
- *Margin.*—Palmately lobed, sinuses between lateral lobes parallel to divergent.
- *Texture of top surface.*—Lightly pubescent.
- *Texture of bottom surface.*—Lightly pubescent.
- *Leaf internode length.*—Approximately 1.2 cm.
- *Color.*—Young foliage upper side: Near Green 137A. Young foliage under side: Near Green 138B. Mature foliage upper side: Near Green 137A. Mature foliage under side: Near Green 137C.
- *Venation.*—Type: Palmately net. Venation color upper side: Near Green 137C. Venation color under side: Near Green 137C.

Petiole:
- *Average length.*—Approximately 1.2 cm.
- *Color.*—Near Green 137A.
- *Diameter.*—Approximately 0.3 cm.

BLOOM

Inflorescence:
- *Flowering habit.*—Induced by darkness period greater than 13.5 hours, approximately 49 days of appropriate day length required to induce and develop blooms.
- *Inflorescence form.*—Daisy.
- *Number of inflorescences per lateral branch.*—Approximately 5.
- *Inflorescence diameter.*—Approximately 7.6 cm.
- *Inflorescence depth.*—Approximately 1 cm.
- *Inflorescence longevity on plant.*—Approximately 35 to 42 days.
- *Inflorescence disc diameter.*—Approximately 1.6 cm.
- *Persistence.*—Persistent.
- *Fragrance.*—None detected.

Ray florets:
- *Appearance.*—Matte.
- *Texture.*—Smooth.
- *Average number of ray florets per inflorescence.*—Approximately 22.
- *Average number of whorls.*—Approximately 2.
- *Shape.*—Oblanceolate.
- *Aspect.*—Flat.
- *Margin.*—Entire.
- *Apex.*—Obtuse.
- *Length.*—Approximately 3 cm.
- *Width.*—Approximately 0.9 cm.
- *Color.*—Upper surface at first opening: Near Red-Purple 74D. Upper surface at maturity: Near Red-Purple 74D. Upper surface at fading: Near Red-Purple 62D. Under surface at first opening: Near Red-Purple 74C. Under surface at maturity: Near Red-Purple 70C. Under surface at fading: Near Red-Purple 62D.

Disc florets:
- *Appearance.*—Shiny.
- *Texture.*—Smooth.
- *Average number of florets per disc.*—Approximately 191.
- *Shape.*—Cylindric.
- *Apex.*—Obtuse.
- *Average length.*—Approximately 0.2 cm.
- *Average width.*—Approximately 0.1 cm.
- *Color.*—At first opening: Near Yellow-Green 154A. At maturity: Near Yellow-Green 154A at center and near Yellow 9A at edge. At fading: Near Yellow-Green 154A at center and near Yellow 9A at edge.

Peduncle:
- *Length.*—At terminal end (shortest): Approximately 3 cm. At lateral end (longest): Approximately 4 cm.
- *Angle to stem.*—Acute.
- *Strength.*—Moderate.
- *Color.*—Near Green 137A.
- *Habit.*—Upright.
- *Diameter.*—Approximately 0.1 cm.
- *Surface texture.*—Lightly pubescent.

Inflorescence bud:
- *Length.*—Approximately 0.4 cm.
- *Diameter.*—Approximately 0.6 cm.
- *Form.*—Globular.
- *Color.*—Near Green 138A.

Involucral bracts (phyllaries):
- *Appearance.*—Matte.
- *Texture.*—Lightly pubescent.
- *Number.*—Approximately 25.
- *Shape.*—Lanceolate.
- *Margin.*—Entire.
- *Apex.*—Obtuse.
- *Length.*—Approximately 0.4 cm.
- *Width.*—Approximately 0.3 cm.
- *Color.*—Upper side: Near Green 137A. Under side: Near Green 137C.

REPRODUCTIVE ORGANS

Ray florets:
- *Number of pistils per floret.*—1.
- *Stigma shape.*—2 branched.
- *Stigma color.*—Near Yellow 9A.
- *Style color.*—Near Yellow-Green 145B.
- *Style length.*—Approximately 0.3 cm.
- *Stamens.*—Absent.

Disc florets:

*Number of pistils per floret.*—1.

*Stigma shape.*—Cylindric.

*Stigma color.*—Near Yellow 9A.

*Style length.*—Approximately 0.2 cm.

*Style color.*—Near Yellow-Green 149C.

*Number of stamens per floret.*—Approximately 5.

*Anther shape.*—Tubular.

*Anther color.*—Near Yellow 9A.

*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'GG GOSTRNG 08' as herein illustrated and described.

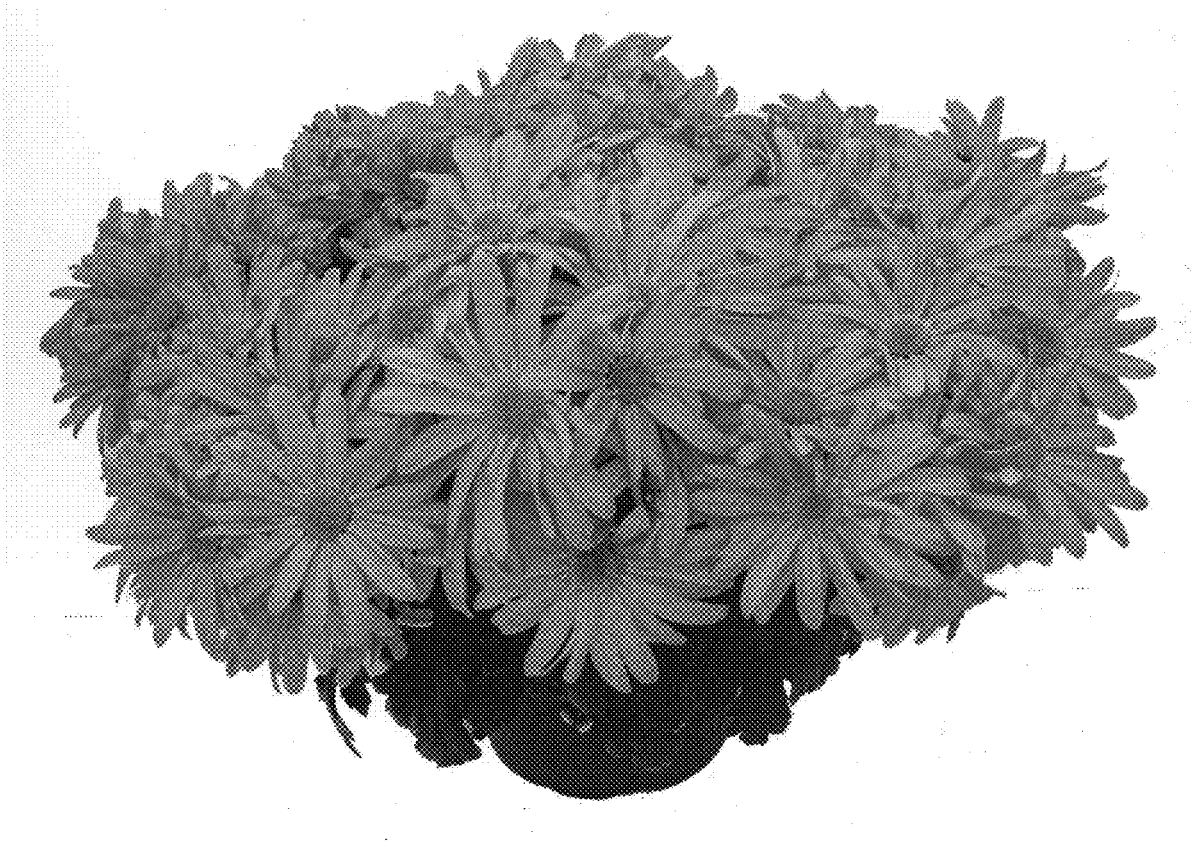

* * * * *